United States Patent
Crane et al.

(10) Patent No.: US 9,970,940 B2
(45) Date of Patent: May 15, 2018

(54) BARRIER LAYER FOR GLUCOSE SENSOR

(75) Inventors: Barry Crane, Oxfordshire (GB);
William Paterson, Oxfordshire (GB);
Nicholas Paul Barwell, Coventry (GB);
Bruce Culbert, Bucks (GB)

(73) Assignee: Lightship Medical Limited, London (GB)

( * ) Notice: Subject to any disclaimer, the term of this patent is extended or adjusted under 35 U.S.C. 154(b) by 965 days.

(21) Appl. No.: 14/239,132

(22) PCT Filed: Aug. 8, 2012

(86) PCT No.: PCT/GB2012/051921
§ 371 (c)(1),
(2), (4) Date: Jul. 28, 2014

(87) PCT Pub. No.: WO2013/024260
PCT Pub. Date: Feb. 21, 2013

(65) Prior Publication Data
US 2014/0349307 A1   Nov. 27, 2014

Related U.S. Application Data

(60) Provisional application No. 61/524,525, filed on Aug. 17, 2011.

(51) Int. Cl.
*G01N 33/551* (2006.01)
*G01N 33/66* (2006.01)
(Continued)

(52) U.S. Cl.
CPC ......... *G01N 33/66* (2013.01); *G01N 21/7703* (2013.01); *G01N 33/582* (2013.01);
(Continued)

(58) Field of Classification Search
None
See application file for complete search history.

(56) References Cited

U.S. PATENT DOCUMENTS 9,151,764 B2 * 10/2015 Crane ................ A61B 5/14532
2005/0173245 A1   8/2005 Feldman et al.
2007/0014726 A1   1/2007 Merical et al.

FOREIGN PATENT DOCUMENTS

| WO | 2004/007756 | 1/2004 |
| WO | 2010/123972 | 10/2010 |
| WO | 2011/097586 | 8/2011 |

OTHER PUBLICATIONS

International Search Report in International Application No. PCT/GB2012/051921, dated Nov. 16, 2012, 4 pages.
(Continued)

*Primary Examiner* — Chris L Chin
(74) *Attorney, Agent, or Firm* — Fish & Richardson P.C.

(57) ABSTRACT

An optical glucose sensor for detecting and/or quantifying the amount of glucose in a sample comprising:
  a sensing region comprising a boronic acid receptor for binding to glucose and a fluorophore associated with said receptor;
  an optical waveguide for directing incident light onto the sensing region; and
  a glucose-permeable barrier layer comprising a semi-permeable membrane having pores and a hydrophilic polymer within the pores of the semi-permeable membrane, the barrier layer overlying at least a part of the sensing region;
wherein the sensor is adapted so that glucose enters the sensing region of the sensor through the glucose-permeable barrier layer, and an ROS-quenching agent is present in the sensing region and/or the glucose-permeable barrier layer.

15 Claims, 4 Drawing Sheets

(51) Int. Cl.
*G01N 21/77* (2006.01)
*G01N 33/58* (2006.01)
*G01N 21/64* (2006.01)

(52) U.S. Cl.
CPC . *G01N 21/6428* (2013.01); *G01N 2021/6434* (2013.01); *G01N 2021/772* (2013.01); *G01N 2021/7786* (2013.01); *Y10T 29/49* (2015.01)

(56) References Cited

OTHER PUBLICATIONS

Oishi et al., "ph-responsive PEGylated nanogel containing platinum nanoparticles: Application to on-off regulation of catalytic activity for reactive oxygen species," Reactive & Functional Polymers, Apr. 2007, 67: 662-668.

\* cited by examiner

Comparison of sensors with 10% PSM (of monomer weight) vs controls without PSM added to the hydrogel and run in human plasma.

BARRIER LAYER FOR GLUCOSE SENSOR

CROSS-REFERENCE TO RELATED APPLICATIONS

This application is the U.S. national stage under 35 USC § 371 of International Application Number PCT/GB2012/051921, filed on 8 Aug. 2012, which claims priority to U.S. Application No. 61/524,525, filed on 17 Aug. 2011, the entire contents of which is hereby incorporated by reference.

FIELD

This document describes glucose sensors, methods for making such glucose sensors, and methods for detecting or determining the quantity of glucose in a sample.

BACKGROUND

It has been known for some time that boronates form reversible 5 membered ring complexes with saccharides. More recently, this property of boronates has been utilized in the development of sensors for the measurement of glucose in biological fluids. For example, a sensor may comprise a glucose receptor (the boronic acid) and a fluorophore that acts as the transmitter of the signal. These indicator chemistries can readily be immobilised onto an optical fibre of appropriate diameter, which can then be placed into body fluids or tissue to measure glucose.

It has been known for some time that boronic acids reversibly complex with glycosylated and glycated proteins. Although attempts have been made to devise sensing boronic acid chemistries that are selective it is obvious that glycated proteins represent potential interferents in the determination of glucose in body fluids when boronic acids are used as the sensor. Also other middle to high molecular weight endogenous materials have the potential to interfere with the boronic acid receptor by acting as quenchers of the transmitting fluorophore.

Further, although little has been known about the normal levels of reactive oxygen species (ROS) such as hydrogen peroxide ($H_2O_2$) in the blood, it is thought that residual levels of ROS normally present in the blood are very low, and thus the potential of ROS as a possible interferent in the determination of glucose in body fluids when boronic acids are used as the sensor has not previously been considered.

SUMMARY

Under oxidative stress, it has been found that levels of ROS such as $H_2O_2$ can rise. Oxidative stress can arise as a result of an ischemic event or sepsis (e.g. as a result of multi-organ failure) and is also implicated in many diseases (e.g. atherosclerosis, Parkinson's disease, heart failure, myocardial infarction, Alzheimer's disease, schizophrenia, bipolar disorder, fragile X syndrome and chronic fatigue syndrome), thereby raising levels of ROS in the body fluids or tissue of subjects who may require their glucose levels to be monitored, for example in an intensive care environment. ROS has been found to oxidise phenyl boronic acids to phenols, which can adversely affect the operation of glucose sensors using boronic acid indicating chemistry.

The presently described glucose sensors and methods therefore address the problem of glycosylated and glycated proteins, other middle to high molecular weight endogenous materials, and ROS interfering with glucose sensor indicating chemistry.

The above-described problem can be addressed by sheathing the boronic acid/fluorophore glucose indicating chemistry with a protective barrier layer which is permeable to glucose but which restricts the passage of large molecular weight molecules such as proteins and glycated proteins, and further by providing an ROS-quenching agent in the sensing region and/or in the barrier layer. Accordingly, the presently described glucose sensors include

- a sensing region comprising a boronic acid receptor for binding to glucose and a fluorophore associated with said receptor;
- an optical waveguide for directing incident light onto the sensing region; and
- a glucose-permeable barrier layer including a semi-permeable membrane having pores and a hydrophilic polymer within the pores of the semi-permeable membrane, the barrier layer overlying at least a part of the sensing region;

wherein the sensor is adapted so that glucose enters the sensing region of the sensor through the barrier layer, and an ROS-quenching agent is present in the sensing region and/or the barrier layer.

The barrier layer is capable of restricting the passage of proteins and glycated proteins into the sensing region. In some embodiments, the barrier layer is substantially impermeable to proteins and glycated proteins. For example, the barrier layer may restrict or prevent the passage of, or be substantially impermeable to, molecules having a molecular weight of greater than 6000, preferably greater than 5000, more preferably greater than 4000.

The barrier layer can include a semi-permeable membrane, for example a dialysis membrane. The pore size of the membrane can be selected so as to ensure permeability to glucose but to restrict or prevent the passage of larger macromolecules such as proteins and glycated proteins. Use of a dialysis membrane having a molecular weight cut off (MWCO) of from 1000 to 5000 eliminates potential interferents such as insulin, beta-microglobulin and albumin and their glycated derivatives.

A hydrophilic polymer can be present within the pores of the membrane. This can be achieved via in situ polymerisation, within the pores of the membrane, of a monomer mixture comprising one or more hydrophilic monomers and optionally one or more negatively charged monomers. The resulting membrane is particularly effective as a barrier to proteins and glycated proteins due to its hydrophilicity and/or negative charge and has the further advantage that the polymerisation process may be used to control, and to further decrease, the pore size of the membrane.

The ROS-quenching agent restricts or preferably prevents ROS from interfering with the boronic/acid fluorophore receptor chemistry, typically by catalysing the decomposition of ROS into chemical species which do not interfere with boronic acid/fluorophore sensor chemistry. The sensing region and/or barrier layer is typically coated and/or impregnated with the ROS-quenching agent.

The presently described method also can include detecting or quantifying the amount of glucose in a sample, inserting into the sample a glucose sensor as described herein, providing incident light to the sensing region of the sensor, and detecting the emission pattern of the fluorophore.

Further preferred features and embodiments are described in the accompanying description and the appended claims.

DETAILED DESCRIPTION

As used herein the term hydrophilic indicates a material which has an affinity for water. The glucose sensors described herein can be used to detect or quantify glucose in an aqueous solution. The hydrophilic barrier layer on the outside of the sensing region therefore has an affinity for the aqueous solution in which the glucose is dissolved. Further, the hydrophilicity of the barrier layer assists in repelling plasma proteins when a sensor is used in a bodily fluid, in particular in blood.

As used herein a glucose permeable barrier layer is a material which allows the passage of glucose through the layer but which restricts the passage of proteins and glycated proteins.

In some embodiments, the ROS-quenching agent is present within the pores of the barrier layer. For example, it may be immobilised within the hydrophilic polymer present within the pores of the semi-permeable membrane. The ROS-quenching agent may be covalently bound to the hydrophilic polymer or it may be present as a separate chemical species.

The glucose permeable barrier layer can be used with any optical glucose sensor using boronic acid/fluorophore glucose sensing chemistry. Fibre optic sensors are particularly envisaged, but the presently described glucose permeable barrier layer may also be used with sensors having different types of optical waveguide. Glucose sensing is typically carried out in bodily fluids such as interstitial tissue or blood, although sensing of any aqueous solution may be carried out. The particular embodiments described herein are envisaged for use as invasive sensors for insertion into a blood vessel. However, the presently described sensors are not limited to such invasive sensors. Non-invasive sensors for in vitro use, implantable sensors, and subcutaneous sensors are also contemplated.

Figure 1:
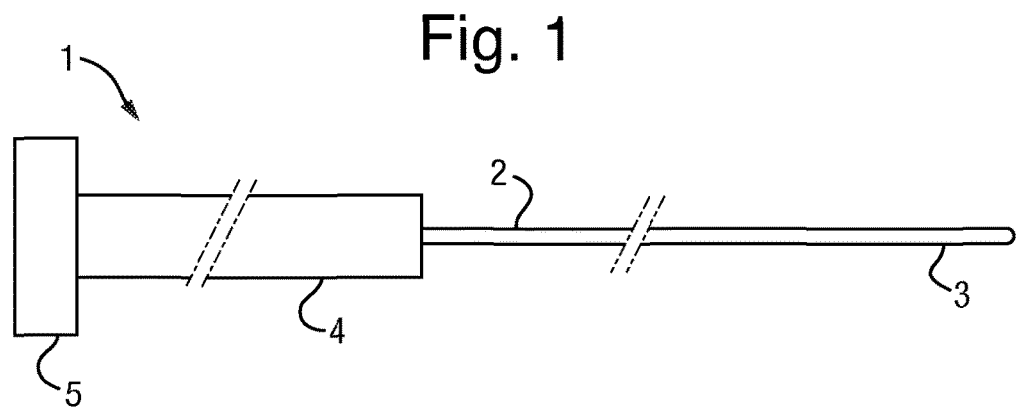
FIGS. 1 and 1a depict a sensor incorporating an optical fibre and a monitor for such a sensor.
Figure 1A:
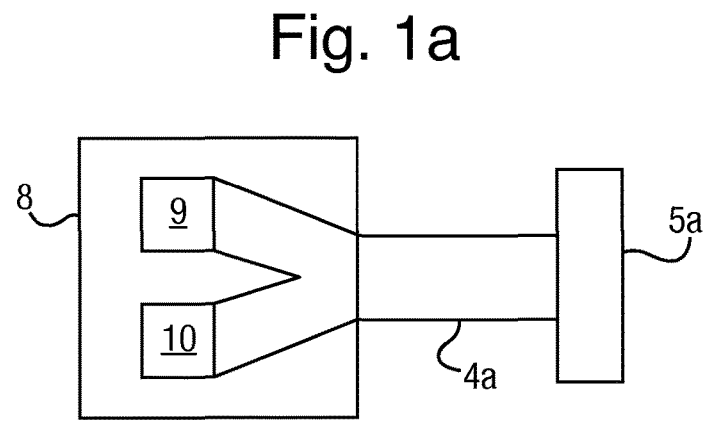

An example of a sensor incorporating an optical fibre is depicted in FIGS. 1 and 1*a*. The sensor 1 comprises an optical fibre 2 including a sensing region 3 at its distal end. In the case of an invasive sensor, fibre 2 is adapted for insertion into a patient, for example insertion into a blood vessel through a cannula. The sensing region 3 (depicted in more detail in FIGS. 2, 3 and 3*a*) contains a cell or chamber 7 in which the indicator chemistry is contained. The optical fibre extends through cable 4 to connector 5 which is adapted to mate with an appropriate monitor 8. The monitor typically includes further optical cable 4*a* that mates with the connector at 5*a* and at the other bifurcates to connect to (a) an appropriate source of incident light for the optical sensor 9 and (b) a detector for the return signal 10.

In some embodiments, the sensor is a disposable sensor. A disposable sensor can be adapted to be connected to a non-disposable monitor comprising a light source 9 and detector 10.

Figure 2:
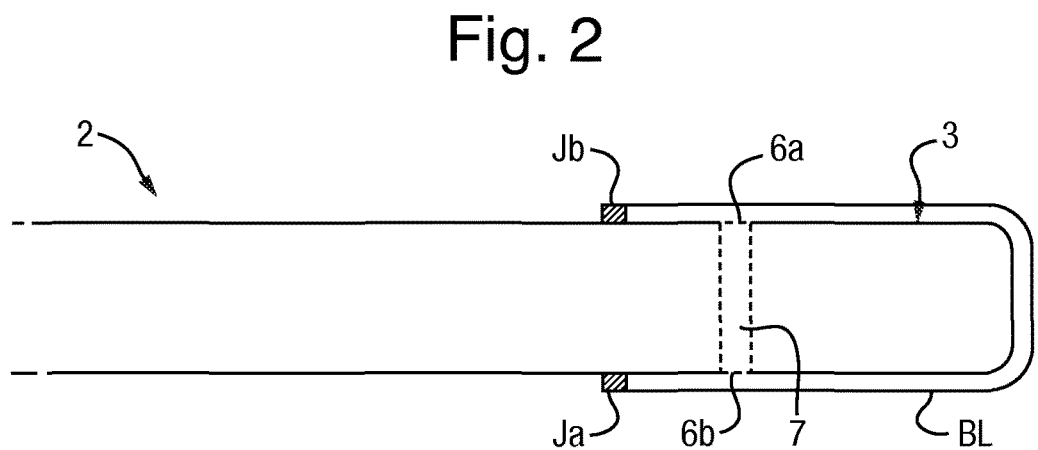
FIGS. 2, 3, and 3*a* depict various embodiments of a sensing region of a sensor.

As depicted in FIG. 2, the sensing region 3 incorporates a cell 7 in the form of a chamber within the fibre. The cell may take any form, as long as it enables the indicator chemistry to be contained in the path of the incident light directed by the waveguide, here a fibre. Thus, the cell may be attached to the distal end of the fibre or waveguide or may be in the form of a chamber within the fibre having any desired shape.

The cell 7 contains the indicator chemistry, namely a boronic acid receptor for binding glucose and a fluorophore associated with the receptor. The emission pattern (e.g. the wavelength, intensity, lifetime) of the fluorophore is altered when the analyte is bound to the receptor allowing optical detection of glucose. The receptor and fluorophore may be directly bonded to one another as a receptor-fluorophore construct. Examples of suitable fluorophores include anthracene, pyrene and derivatives thereof. Examples of suitable boronic acid receptors are compounds having at least one, preferably two boronic acid groups.

In a preferred embodiment, the receptor is a group of formula (I)

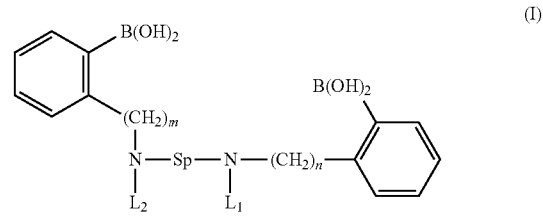

wherein m and n are the same or different and are typically one or two, preferably one; Sp is an alphatic spacer, typically an alkylene moiety, for example a C1-C12 alkylene moiety, e.g. a C6 alkylene moiety; and L1 and L2 represent possible points of attachment to other moieties, for example to a fluorophore or to a hydrogel. For example, L1 and L2 may represent an alkylene, alkylene-arylene or alkylene-arylene-alkylene moiety, linked to a functional group. Where no attachment to another moiety is envisaged, the functional group is protected or replaced by a hydrogen atom. Typical alkylene groups for L1 and L2 are C1-C4 alkylene groups, e.g. methylene and ethylene. Typical arylene groups are phenylene groups. The functional group is typically any group which can react to form a bond with, for example, the fluorophore or hydrogel, e.g. ester, amide, aldehyde or azide.

Varying the length of the spacer Sp alters the selectivity of the receptor. Typically, a C6-alkylene chain provides a receptor which has good selectivity for glucose.

Further details of such receptors are found in U.S. Pat. No. 6,387,672, the contents of which are incorporated herein by reference in their entirety.

Further examples of receptors suitable for the presently described sensors include those of formula (II):

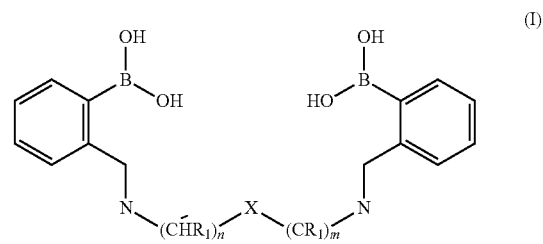

wherein X represents O, S, $NR_2$ or $CHR_3$;
n is from 1 to 4;
m is from 1 to 4, and n+m is 5;
$R_2$ represents hydrogen or $C_{1-4}$ alkyl;
each $R_1$ is the same or different and represents hydrogen, $C_{1-4}$ alkyl or $C_{3-7}$ cycloalkyl;
or $R_1$, together with an adjacent $R_1$, $R_2$ or $R_3$ group and the carbon or nitrogen atoms to which they are attached, form a $C_{3-7}$ cycloalkyl or a 5- or 6-membered heterocyclyl group, wherein when X represents $CHR_3$, $R_3$ together with an adjacent $R_1$ group and the carbon atoms to which they are attached form a $C_{3-7}$ cycloalkyl group. Further details of receptors of this type are found in U.S. 61/431,756, the contents of which are incorporated herein by reference.

The receptor and fluorophore are typically bound to one another and may further be bound to a polymeric matrix such as a hydrogel, or to a dendrimer. Examples of suitable hydrogels and dendrimers are those described in PCT/GB2011/000207, the content of which is incorporated herein by reference. In some embodiments the receptor and fluorophore are bound to one another and to a hydrogel which is a co-polymer obtainable from co-monomers wherein one or more (e.g. one) co-monomer is an ionic co-monomer (e.g a negatively charged co-monomer). An example of a suitable negatively charged co-monomer is potassium sulphopropyl methacrylate (PSM).

In some embodiments, the ROS-quenching agent is present within the sensing region. The ROS-quenching agent may be present in the sensing region as a separate chemical species, or may be bound covalently to the polymeric matrix such as a hydrogel, or to a dendrimer. Suitable ROS-quenching agents are described herein.

Figure 3:
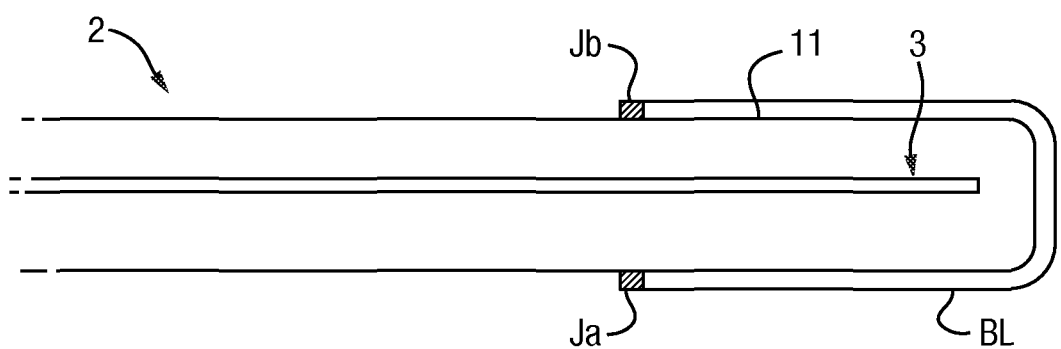
Figure 3A:
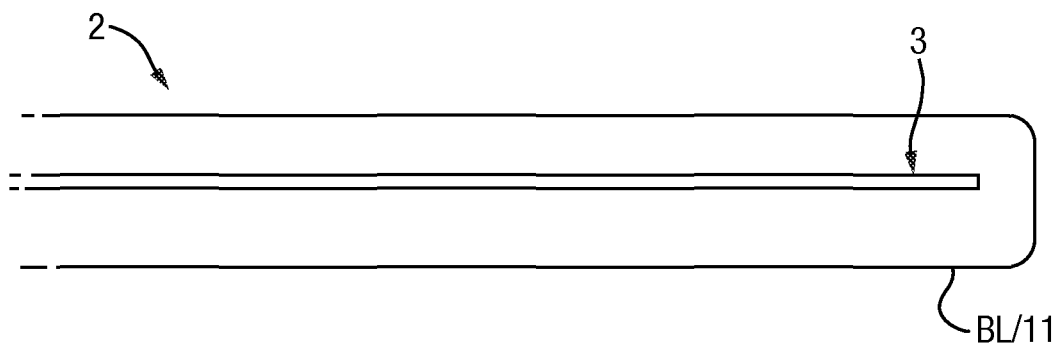

The sensing region 3 of the glucose sensor has one or more openings 6a, 6b to enable glucose to enter the cell. The barrier layer can be provided across these openings so that glucose enters the cell through the barrier layer. In FIGS. 2, 3 and 3a, the barrier layer is provided over the entire sensing region 3. Alternatively, however, the barrier layer may be provided on only part of the sensing region, for example only across openings 6a and 6b.

The sensor is typically designed such that any openings into the sensing region through which glucose can pass are covered with the barrier layer. This ensures that protein adsorption is restricted at least at the openings into the sensing region. Further, when the ROS-quenching agent is present in the barrier layer, this arrangement ensures that ROS does not interfere with the boronic acid/fluorophore chemistry by restricting or preventing passage of ROS into the sensing region. In a preferred embodiment, however, the entire sensing region, or the entire surface of the sensor which is to come into contact with the sample under test, is coated or sheathed with the barrier layer. This helps to prevent protein adsorption on any surface of the sensor and improves the biocompatibility of the sensor in the case of invasive or implantable sensors.

As depicted in FIG. 2, the barrier layer BL may be applied directly onto the sensing region, here onto the tip of the optical fibre. In an alternative embodiment depicted in FIG. 3, the sensing region 3 is provided within a separate support 11 and the barrier layer is provided on the support 11. The use of a separate support structure provides additional strength to the barrier layer which may itself be fragile. Holes or pores are provided in the support to enable glucose to enter the sensing region 3.

Suitable support structures are polymer tubes which are perforated with holes, for example by laser ablation. Microporous hollow fibres which are commonly used in medical oxygenators and which have pores of approximately 0.2 micron in diameter provide appropriate support structures for use with fibre optic sensors. Alternative support structures are woven sheaths of polymeric or metallic materials such as those described in WO2009/019470, the contents of which are incorporated herein by reference in their entirety.

In some embodiments, such as depicted in FIG. 3a, the barrier layer itself may form the support structure (BL/11). The membrane used to form this barrier layer can be a microporous hollow fibre membrane.

If desired, the barrier layer may be adhered to the surface of the sensor e.g. to the optical fibre itself or to support 11. This can be achieved by application of a suitable adherent such as cyanoacrylate. Alternatively, where the sensor surface and the barrier layer material are appropriate, the joint between the barrier layer and the sensor can be thermoformed, e.g. at Ja, Jb of FIGS. 2 and 3.

The barrier layer can be formed from a polymeric, semi-permeable membrane material which is hydrophilic, permeable to glucose and which offers some restriction to the passage of high molecular weight materials such as proteins.

In some embodiments, the semi-permeable membrane is a dialysis membrane. Dialysis membranes are semi-permeable membranes that separate molecules by virtue of their size, shape, hydration and polarity. They are particularly suitable for use in the presently described protective barrier layer since their pore size allows glucose to permeate the membrane but is too small to allow the passage of proteins. Dialysis membranes are usually in the form of hollow fibres and are available in materials such as polyarylethersulphone, polyamide, polycarbonate, polyacrylonitrile, polysulphone, polyethersulphone, polyvinylidenefluoride and cellulosic materials or mixtures or modifications thereof.

In other embodiments, the semi-permeable membrane is formed from a microporous membrane. Microporous membranes suitable for use in this aspect typically have a pore size in the region of 0.1 to 10 μm, e.g. up to 2 μm or up to 1 μm, for example about 0.2 μm. Preferred examples of microporous membranes include polypropylene hollow fibre membranes. Polypropylene hollow fibre membranes are known in the art.

The semi-permeable membrane has a hydrophilic polymer incorporated within the pores of the membrane (e.g. by in situ polymerisation within the pores). The presence of the polymer within the pores causes a reduction in the pore size such that the membrane forms a barrier to high molecular weight materials such as proteins and glycated proteins.

Semi-permeable membranes are available with different pore sizes relating to the molecular weight cut-off (MWCO) of the membrane. The molecular weight cut-off indicates the maximum molecular weight of molecule which can pass through the pores of the membrane. Small pore sizes are termed "low flux" with a low MWCO and a larger pore size is termed "high flux" with a high MWCO. Proteins are macromolecules that range in molecular weight from around 6,000 for insulin to 11,800 for beta-microglobulin, 66,200 for albumin to 970,000 for IGN. Thus to eliminate these potential interferents and their derivatives a low MWCO material should be chosen that does not allow materials of molecular weight 6,000 or higher to pass through but does allow glucose (MW180) to pass. The pore size should, however, be maximised whilst eliminating these interferents in order to provide a maximum flux of glucose into the sensor.

In order to provide an acceptable response time for an intravascular sensor which continuously measures glucose, the membrane should preferably be selected so as to provide a 90% response time of no more than three minutes, preferably no more than two-and-a-half minutes. Preferred membranes have a MWCO of at least 1,000 and preferably no more than 5,000. For example, the MWCO may be at least 1,500 or at least 2,000, for example no more than 4,000. Preferred pore sizes are 1 to 20 nm, preferably 1 to 10 nm, for example about 6 nm.

In the embodiment described below in which polymerisation is carried out within the pores of the membrane, the polymerisation step decreases the effective MWCO and pore size of the membrane. The preferred MWCO and pore sizes described above refer to the final membrane for use in the glucose sensor and are therefore the effective MWCO and effective pore sizes of the resulting membrane following in situ polymerisation.

The sensor may be directly coated or sheathed with the membrane, but it is preferred that the membrane is provided on a support, e.g. a tube into which the sensor is placed (see FIG. 3).

Some of the materials used as semi-permeable membrane materials are inherently hydrophobic, for example polysulphone, polyethersulphone and polyvinylidenefluoride. In accordance with some embodiments, the barrier layer is hydrophilic in order to avoid adsorption of serum proteins onto the layer. Materials which are by nature hydrophobic are therefore modified in order to provide some hydrophilic character A hydrophilic character can be provided by using a hydrophilic polymer, typically having functional groups with known protein repelling characteristics, within the pores of the membrane.

The provision of the polymer within the pores of the membrane can be achieved by diffusing one or more suitable hydrophilic monomers into the membrane and initiating polymerisation, for example by applying UV activation in the presence of an initiator. This leads to polymerisation occurring within the pores of the membrane and the resulting polymer is trapped within the pores. If desired, the diffusion and polymerisation steps can be repeated one or more times to increase the amount of polymer formed within the membrane pores. The membrane is, for example, in the form of a hollow fibre dialysis membrane such that the resultant tube could be used to sheath the sensor providing the necessary barrier properties.

In some embodiments, the polymer formed within the pores of the membrane is a hydrogel. A hydrogel as used herein is a hydrophilic polymeric matrix which swells when placed in water. When placed in water, water is dispersed throughout the matrix. Examples of suitable hydrogel materials include cross-linked polyacrylamide, polydimethyl acrylamide, poly hydroxyl ethylmethacylate, polyvinyl pyrrolidone, poly ethylene glycol acrylates and poly ethylene glycol methacrylates.

The hydrophilic polymer can have functional groups with known protein repelling characteristics. Examples of such functional groups integrated into the membrane (e.g. mircroporous membrane or dialysis membrane) can include polyethylene glycol and polyethylene. Suitable hydrophilic monomers for use in this embodiment therefore include polyethyleneglycol dimethacrylate, polyethyleneglycol dimethacrylamide, polyethylenglycol diacrylate and polyethyleneglycol diacrylamide, or a combination thereof. Polyethyleneglycol dimethacrylate is preferred. Polyethylene glycol dimethacrylate and polyethyleneglycol diacrylate, and various derivatives, of varying molecular weights can be readily obtained from Sigma-Aldrich, UK.

In some embodiments, the monomer mixture which is diffused into the membrane pores comprises a chain extending monomer in addition to the hydrophilic monomer(s). Examples of suitable chain extenders include di(meth)acrylate and di(meth)acrylamide.

Membranes having a hydrophilic polymer present within the pores of the membrane in accordance with these embodiments have been shown to provide significant inhibition to protein adsorption and enhancement as a barrier to boronic acid receptor/fluorophore interferents. In addition, such treated membranes provide the ability to decrease and to fine tune the membrane pore size. Since the hydrophilic monomer(s) are diffused into the pores of the membrane and polymerised in-situ, the pore size will decrease and hence the MWCO will decrease.

This decrease in pore size provides a membrane which acts as a more efficient barrier to proteins and glycated proteins. Hence, by variation of the concentration of the diffusing monomer solution and crosslinker, and the number of times the diffusion and polymerisation is carried out, the pore size and MWCO can be adjusted and determined by experiment. MWCO can be determined by the diffusion of monodisperse materials of known molecular weights with a fluorescent molecule attached. Materials of gradually increasing molecular weight are passed through the membrane and the diffusion breakthrough can be determined using a fluorimeter as a detector. Examples of suitable monodisperse materials are fluorescein-labelled dextrans available from Sigma-Aldrich in a variety of molecular weights.

In a further aspect, the effectiveness of the barrier layer can be enhanced by incorporating a negative charge into the layer. Proteins are negatively charged at physiological pH so the incorporation of a negative charge into the barrier layer acts as a repellent to proteins including glycated proteins, or other negatively charged interferents. This can be achieved by incorporating a negatively charged monomer or polymer into the barrier layer.

Suitable negatively charged monomers or polymers include potassium sulphopropylmethacrylate, acrylic or methacylic acids or their corresponding polymers.

Negatively charged monomers or polymers can be grafted to the membrane itself. Alternatively, one or more negatively charged polymers can be incorporated into the polymer mixture during wet spinning formation of a dialysis membrane. This directly incorporates a negatively charged monomer into the membrane structure. One or more negatively charged polymers may be used alone, or in combination with one or more hydrophilic polymers.

Alternatively, one or more negatively charged monomer(s) such as potassium sulphopropylmethacrylate can be diffused into the membrane (e.g. microporous membrane or dialysis membrane) and then polymerised in situ. Polymerisation can be carried out in a similar manner to that discussed above with regard to hydrophilic monomers such as polyethyleneglycol dimethacrylate. This process leads to the formation of a negatively charged polymer which is trapped by virtue of its size, or through copolymerisation with hydrophilic monomers, within the pores of the membrane (e.g. microporous membrane or dialysis membrane). Such polymerisation may be carried out using one or more negatively charged monomers alone, or using a mixture of one or more hydrophilic monomers as described above and one or more negatively charged monomers.

In an alternative embodiment, the negatively charged material is heparin. This has the advantage that the negative charge carried on the heparin molecule repels proteins, but has the added benefit of being antithrombogenic. Heparin can be grafted to, or polymerised with, a membrane (e.g. microporous membrane or dialysis membrane).

The ROS-quenching agent can be any substance capable of catalysing the decomposition of ROS. Examples of ROS include hydrogen peroxide, lipid peroxides, superoxide, peroxynitrite and singlet oxygen.

Preferably, the ROS-quenching agent is an $H_2O_2$-quenching agent, i.e. an agent capable of catalysing the decomposition of $H_2O_2$.

The decomposition of $H_2O_2$ into chemical species which do not interfere with boronic acid/flurophore sensor chemistry can occur by disproportionation to water and oxygen gas:

$$2H_2O_2 \rightarrow 2H_2O + O_2$$

Suitable substances capable of catalysing the decomposition of $H_2O_2$ into water and oxygen gas include transition metals, transition metal compounds, enzymes and antioxidants. In some embodiments the $H_2O_2$-quenching agent is a transition metal, a transition metal compound, an enzyme, or a combination thereof.

In some embodiments, the ROS-quenching agent is selected from an enzyme, a noble metal, a metal oxide or metal sulphide, an antioxidant, or a combination thereof. For example, the ROS-quenching agent may be an enzyme selected from catalase, glutathionine peroxidise, selenium glutathione peroxidise, superoxide ditmutase, peroxiredoxin and thioredoxin; a noble metal selected from platinum, gold, silver, palladium and alloys and nanoparticles thereof; a metal oxide or sulfide selected from manganese dioxide, ruthenium oxide, ruthenium sulphide, and silver oxide; an antioxidant selected from TEMPOL, vitamin A, retinol, carotenoids (e.g. lycopene carotenes and lutein), limonoid, phytosterol, anthocyanidin, catechin, isoflavone, oligomeric proanthocyanidin, isothiocyanate, dithiolthione, sulforaphane, isoprenoid, vitamin E (e.g. tocotrienols and tocopherol), lipoic acid, ubiquinone-coenzyme Q, vitamin C (e.g. ascorbate), 2,3-dihydro-1-benzofuran-5-ols, chromanone, water-soluble fullerene antioxidant, C60, C70, phenols (e.g. BHT, trolox), polyphenols (e.g. caffeic acid, hydrocaffeic acid, cinnamic acid, benzoic acid, vanillic acid, pyruvate, resveratrol, flavonoids), porphyrin based antioxidants, uric acid, melatonin, and caveolin-1, or a combination thereof. In one aspect of this embodiment, these ROS-quenching agents may be functionalised, for example to facilitate their retention in the barrier layer and/or sensing region of the sensor. In certain embodiments, the ROS-quenching agent may be functionalised to contain a polymerisable group such as a C=C double bond, which enables the quenching agent to be copolymerised within a polymeric matrix.

In other embodiments, the ROS-quenching agent is a transition metal, a transition metal compound, an enzyme, or a combination thereof.

Typically, the transition metal used as the ROS-quenching agent is a metal of Group 10 or 11 of the Periodic Table, e.g. nickel, palladium, platinum, copper, silver, gold, or an alloy thereof. Preferably, the transition metal used as the ROS-quenching agent is platinum, gold, silver, or an alloy thereof, more preferably platinum or a gold/silver alloy, most preferably platinum.

Typically, the transition metal compound used as the ROS-quenching agent is a compound of a metal of Group 7 of the Periodic Table, e.g. a Group 7 oxide, for instance manganese dioxide.

Typically, the enzyme used as the ROS-quenching agent is catalase or superoxide dismutase, preferably catalase.

In a preferred embodiment, the ROS-quenching agent is a metal of Group 10 of the Periodic Table or an enzyme. In a particularly preferred embodiment, the ROS-quenching agent is platinum or catalase. Most preferably the ROS-quenching agent is platinum.

In some embodiments, the ROS-quenching agent comprises a combination of two or more of the above described species.

When the ROS-quenching agent is a transition metal or a transition metal compound, it is typically present in the form of nanoparticles, i.e. particles with a nanoscale average particle size, preferably 3-100 nm, although larger particles (e.g. microparticles) can also be used. Preferably, the particles have an average particle size of 50 nm or larger to aid retention in the barrier layer and/or sensing region.

When the ROS-quenching agent is present in the barrier layer, its effectiveness can be quantified by measuring the time taken for a 25 mm test strip of the barrier layer material to evolve 100 cm$^3$ of oxygen gas from 10 ml of 30% $H_2O_2$. Typically, the time taken for the barrier layers used in the sensor will be 200 seconds or less, preferably 150 seconds or less, more preferably 100 seconds or less and most preferably 50 seconds or less.

In some embodiments, the barrier layer can further comprise the boronic acid receptor and the fluorophore.

The sensor may be manufactured by providing a sensing region comprising a boronic acid receptor for binding to glucose and a fluorophore associated with said receptor; providing an optical waveguide for directing incident light onto the sensing region; and providing a hydrophilic, polymeric, glucose-permeable barrier layer on at least a part of the sensing region; and wherein the sensor is adapted so that glucose enters the sensing region of the sensor through said barrier layer.

In particular embodiments, the method comprises diffusing one or more hydrophilic monomers, optionally one or more negatively charged monomers, and optionally an ROS-quenching agent into the pores of the membrane (e.g. a dialysis membrane or a microporous membrane) and initiating polymerisation. This results in a hydrophilic and optionally negatively charged polymer being formed within the pores of the membrane (e.g. the microporous or dialysis membrane) and a decrease in pore size. Polymerisation to form the hydrophilic and optionally negatively charged polymer can be carried out either before or after applying the membrane (e.g. microporous membrane or dialysis membrane) to the sensing region of the sensor.

In the case of an ROS-quenching agent being incorporated into the monomer mixture described above, this leads to a sensor having the ROS-quenching agent present within the barrier layer. The ROS-quenching agent may be present in the monomer mixture as a separate chemical species (e.g. when the ROS-quenching agent is a transition metal or transition metal compound), may be bound covalently to one or more of the monomers (e.g. when the ROS-quenching agent is an enzyme, or is a particle with an average size smaller than about 50 nm), or may be functionalised and copolymerised with the monomer(s) (e.g. when the ROS-quenching agent has an average size smaller than about 50 nm). When the ROS-quenching agent is a transition metal (e.g. a platinum particle) it may be included in the monomer mixture as part of a hydrophilic complex, preferably with one or more hydrophilic chelating ligands.

In the case of an ROS-quenching agent being present in the sensing region, this can be produced by incorporating the ROS-quenching agent into a monomer mixture used to form a hydrogel containing the receptor and fluorophore.

Reference Example 1

A polyethersulphone hollow fibre dialysis membrane was dipped into a monomer mixture as set out below for 10 minutes and then polymerisation was initiated by UV at 240 nm for 30 seconds at a power setting of 8.3 milliwatts. The resultant membrane was washed in phosphate buffer solution at 37 C for 12 hours, rinsed in distilled water and then air dried.
Monomer Mixture
2.00 g Polyethylene glycoldimethacrylate (600)
1.00 g Dimethylacrylamide
0.50 g Potassium propylsulphomethacrylate
0.02 g Irgacure 651
0.20 g Triton X
3.50 Water The resultant membrane contains a polymer having units derived from dimethyl acrylamide, potassium sulphopropylmethacrylate, and crosslinked with polyethylene glycol dimethacrylate, within its pores.

The sensing region of a fibre optic glucose sensor utilising a diboronic acid/fluorophore indicator in accordance with those described in U.S. Pat. No. 6,387,672 was sheathed with the above membrane and used to determine glucose concentrations of human blood. For comparison, experiments in the same blood samples were also carried out using a sensor identical to that described above except that it is sheathed with unmodified polyethersulphone hollow fibre dialysis membrane.

The sensors were tested by excitation with an appropriate excitation wavelength and measurement of the emission signal from the sensor chemistry. A response curve to glucose was defined by varying the glucose concentration though three points, the curve was further defined by a set of three constants which allows the calculation of glucose concentration at any given measured emission intensity. The modulation is a measure of the intensity change for a given change in the glucose concentration and is hence a measure of the sensitivity of the sensor. An initial modulation was determined at zero time from a 3-point calibration in isotonic phosphate buffered saline and this was compared with modulations calculated from further 3-point calibrations following exposure of the sensors to human blood for both 5 and 20 hours. The results are depicted in FIG. 4.

Figure 4:
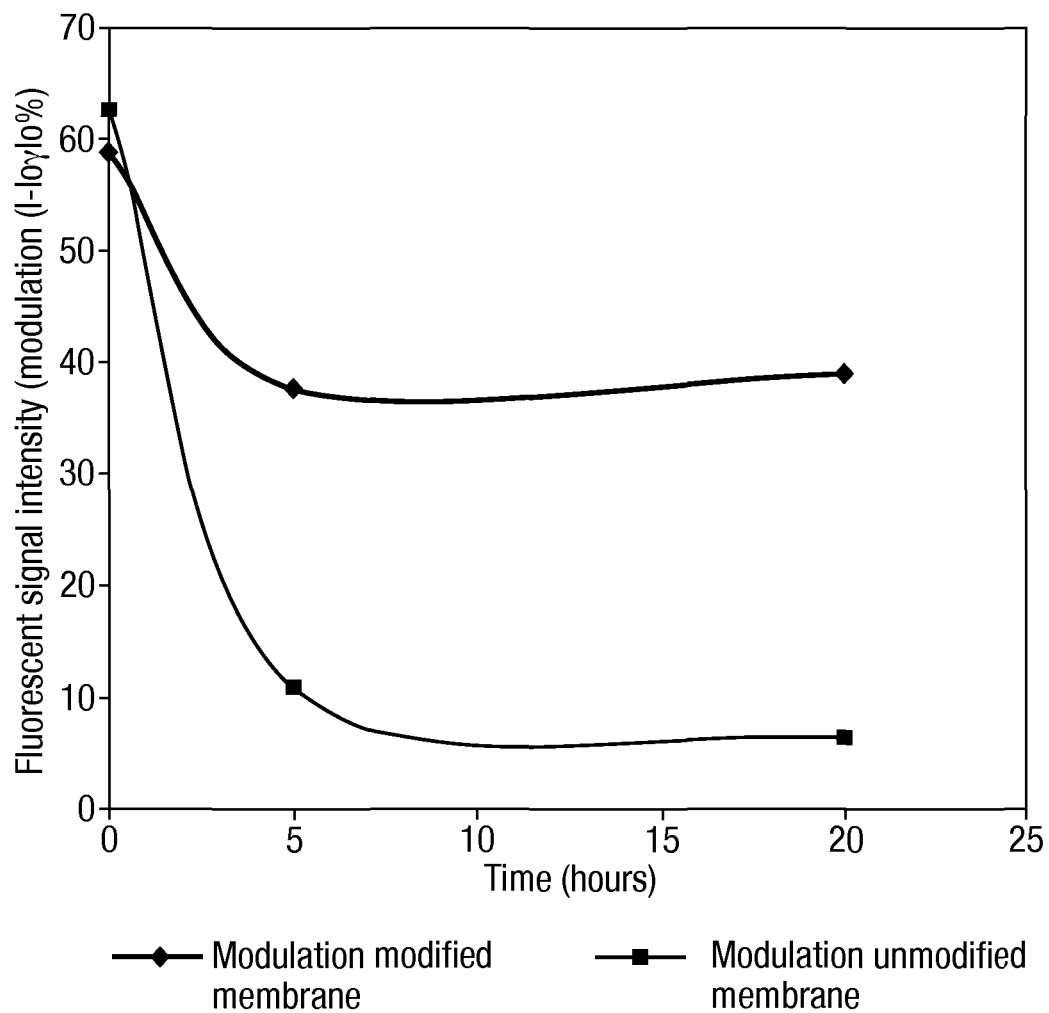
FIG. 4 shows a graph of the glucose calibration of a fibre optic sensor sheathed with a polyether sulphone hollow fibre dialysis membrane which is (a) modified by the in-situ polymerisation process described in Example 1 or (b) unmodified. The calibrations were run in human blood.

FIG. 4 shows comparatively the fluorescent signal intensity of each sensor. It can be seen that the decrease in fluorescent intensity with time is much greater for the sensor that has the unmodified membrane than that for the sensor with the modified membrane. The modified membrane has much better barrier properties to protein and glycated proteins that are present in human blood, resulting in significantly improved sensitivity of the sensor.

Example 1

A sensor having a barrier layer comprising Pt nanoparticles as the ROS-quenching agent is obtained by following the procedure described above for Reference Example 1 but incorporating platinum nanoparticles (available commercially from Sigma-Aldrich, UK) in the monomer mixture.

Example 2

Figure 5:
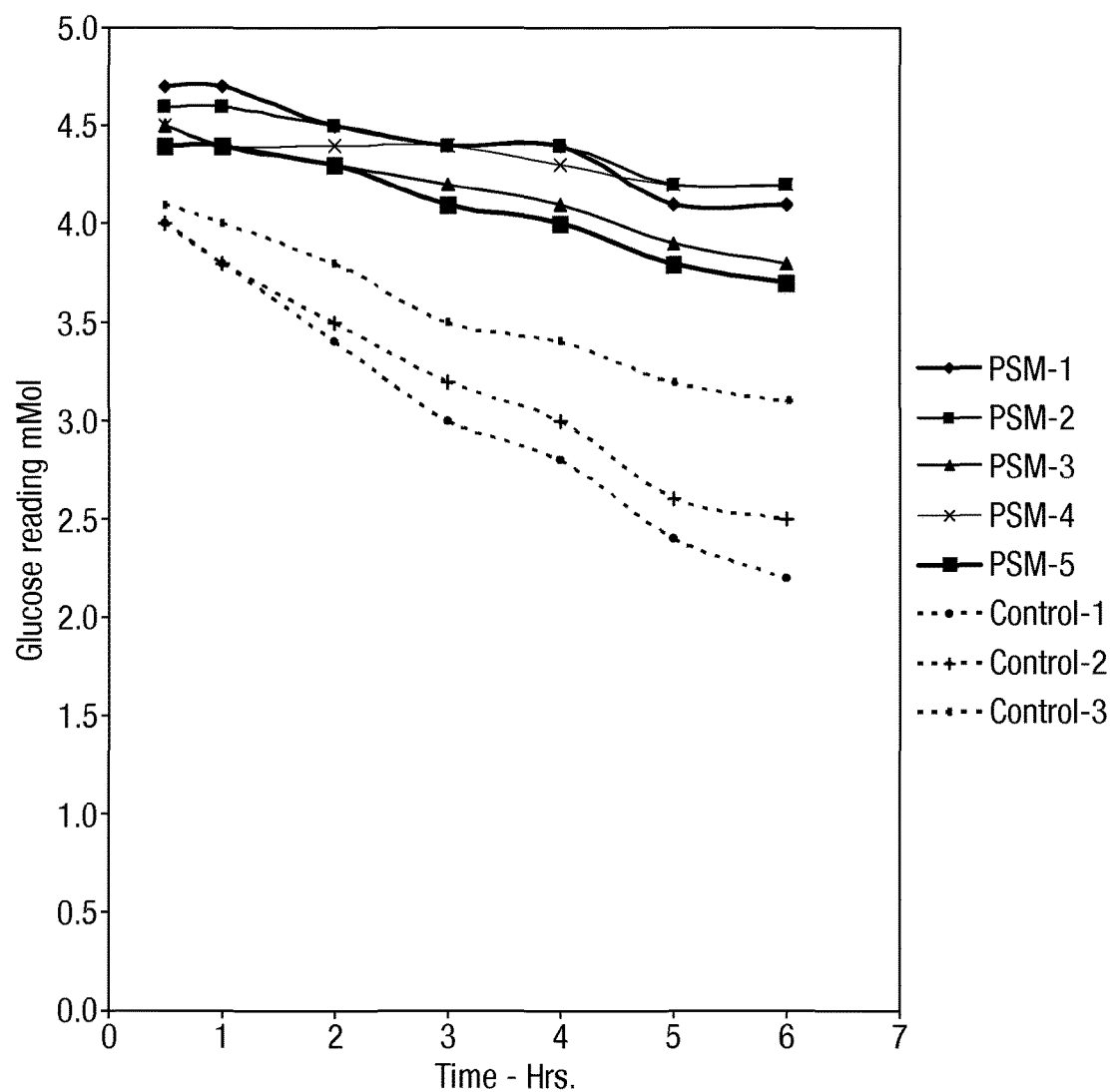
FIG. 5 shows a graph comparing sensors prepared with PSM as an ionic co-monomer in the glucose sensing hydrogel (PSM-1 to PSM-5) to sensors prepared without PSM (Control-1 to Control-3), according to Example 2.

Glucose sensors having a barrier layer comprising Pt nanoparticles as the ROS-quenching agent were prepared with and without potassium sulphopropyl methacrylate (the ionic comonomer PSM) as a constituent of the glucose sensing hydrogel. Both types of sensors were calibrated and then run for six hours in human plasma at a constant temperature of 37° C. The results are shown in FIG. 5. Sensors with PSM were subject to significantly less drift than those without.

Sensors having barrier layers have been described with reference to a number of particular embodiments and examples. The claims, however, are not limited to these specific embodiments and examples.

The invention claimed is:

1. A glucose sensor for detecting and/or quantifying the amount of glucose comprising:
   a sensing region comprising a boronic acid receptor for binding to glucose and a fluorophore associated with the boronic acid receptor;
   an optical waveguide for directing light onto the sensing region; and
   a glucose-permeable barrier layer comprising a semi-permeable membrane comprising pores and a hydrophilic polymer within the pores of the semi-permeable membrane, the glucose-permeable barrier layer overlying at least a part of the sensing region;
   wherein the glucose enters the sensing region of the sensor through the glucose-permeable barrier layer, and an ROS-quenching agent which is platinum in the form of nanoparticles is present in the glucose-permeable barrier layer.

2. A glucose sensor according to claim 1, wherein the semi-permeable membrane restricts the passage of proteins and glycated proteins having a molecular weight of 6000 or greater.

3. A glucose sensor according to claim 1, wherein the semi-permeable membrane restricts the passage of proteins and glycated proteins having a molecular weight of 5000 or greater.

4. A glucose sensor according to claim 1, wherein the semi-permeable membrane has an effective pore size of from 1 to 20 nm.

5. A glucose sensor according to claim 1, wherein a negatively charged polymer is present within the pores of the membrane.

6. A glucose sensor according to claim 1, wherein the semi-permeable membrane is formed by generating the hydrophilic and optionally the negatively charged polymer in situ by diffusing a monomer mixture comprising one or more hydrophilic monomer(s), optionally one or more negatively charged monomer(s) and optionally an ROS-quenching agent into the pores of a membrane and initiating polymerisation.

7. A glucose sensor according to claim 1, wherein the ROS-quenching agent is immobilised within the hydrophilic polymer which is present within the pores of the membrane.

8. A glucose sensor according to claim 1, wherein the hydrophilic polymer present within the pores of the semi-permeable membrane is a hydrogel.

9. A glucose sensor according to claim 1, wherein the barrier layer comprises heparin.

10. A glucose sensor according to claim 1, wherein the membrane is a microporous membrane and the barrier layer forms a support structure on the sensing region.

11. A method of manufacturing a glucose sensor for detecting and/or quantifying the amount of glucose comprising:

a sensing region comprising a boronic acid receptor for binding to glucose and a fluorophore associated with the boronic acid receptor;

an optical waveguide for directing light onto the sensing region; and a glucose-permeable barrier layer comprising a semi-permeable membrane comprising pores and a hydrophilic polymer within the pores of the semi-permeable membrane, the glucose-permeable barrier layer overlying at least a part of the sensing region;

wherein the glucose enters the sensing region of the sensor through the glucose-permeable barrier layer, and an ROS-quenching agent which is platinum in the form of nanoparticles is present in the glucose-permeable barrier layer;

wherein the method comprises providing a sensing region comprising a boronic acid receptor for binding to glucose and a fluorophore associated with said receptor;

providing an optical waveguide for directing incident light onto the sensing region; and providing a glucose-permeable barrier layer comprising a semi-permeable membrane having pores and a hydrophilic polymer within the pores of the semi-permeable membrane, the glucose-permeable barrier overlying at least a part of the sensing region;

wherein the glucose enters the sensing region of the sensor through the glucose-permeable barrier layer, and an ROS-quenching agent which is platinum in the form of nanoparticles is present in the glucose-permeable barrier layer.

12. A method according to claim 11, wherein the method comprises diffusing a monomer mixture comprising one or more hydrophilic monomer(s), an ROS-quenching agent which is platinum in the form of nanoparticles and optionally one or more negatively charged monomer(s) into the pores of a membrane and initiating polymerisation, to provide a semi-permeable membrane comprising an ROS-quenching agent and a hydrophilic and optionally negatively charged polymer within the pores of the membrane.

13. A method according to claim 11, wherein the polymer formed within the pores of the membrane is a hydrogel.

14. A method according to claim 13, wherein the monomer mixture further comprises a boronic acid receptor and a fluorophore.

15. A method of detecting and/or quantifying the amount of glucose in a sample, the method comprising:

inserting into the sample a glucose sensor;

providing incident light to the sensing region of the sensor; and detecting an emission pattern of a fluorophore associated with a boronic acid receptor for binding to glucose;

wherein the glucose sensor comprises:

a sensing region comprising the boronic acid receptor and the fluorophore associated with the boronic acid receptor;

an optical waveguide for directing light onto the sensing region; and a glucose-permeable barrier layer comprising a semi-permeable membrane comprising pores and a hydrophilic polymer within the pores of the semi-permeable membrane, the glucose-permeable barrier layer overlying at least a part of the sensing region;

wherein the glucose enters the sensing region of the sensor through the glucose-permeable barrier layer, and an ROS-quenching agent which is platinum in the form of nanoparticles is present in the glucose-permeable barrier layer.

* * * * *